(12) United States Patent
Kilgore et al.

(10) Patent No.: US 9,403,014 B2
(45) Date of Patent: Aug. 2, 2016

(54) ONSET-MITIGATING HIGH-FREQUENCY NERVE BLOCK

(71) Applicant: Case Western Reserve University, Cleveland, OH (US)

(72) Inventors: Kevin L. Kilgore, Avon Lake, OH (US); Niloy Bhadra, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/626,992

(22) Filed: Feb. 20, 2015

(65) Prior Publication Data

US 2015/0165210 A1    Jun. 18, 2015

Related U.S. Application Data

(62) Division of application No. 12/739,413, filed as application No. PCT/US2008/012209 on Oct. 28, 2008, now Pat. No. 8,983,614.

(60) Provisional application No. 60/983,420, filed on Oct. 29, 2007.

(51) Int. Cl.
  *A61N 1/36* (2006.01)
  *A61N 1/20* (2006.01)
  *A61N 1/32* (2006.01)

(52) U.S. Cl.
  CPC ............ *A61N 1/36171* (2013.01); *A61N 1/205* (2013.01); *A61N 1/32* (2013.01); *A61N 1/3615* (2013.01); *A61N 1/36057* (2013.01); *A61N 1/36067* (2013.01); *A61N 1/36071* (2013.01); *A61N 1/36103* (2013.01); *A61N 1/36167* (2013.01)

(58) Field of Classification Search
  CPC .................................................. A61N 1/36071
  See application file for complete search history.

(56) References Cited

U.S. PATENT DOCUMENTS

| | | | |
|---|---|---|---|
| 6,275,735 B1 | 8/2001 | Jarding et al. | |
| 7,389,145 B2 | 6/2008 | Kilgore et al. | |
| 2004/0147977 A1 | 7/2004 | Petrofsky | |
| 2005/0131485 A1 | 6/2005 | Knudson et al. | |
| 2005/0137648 A1 | 6/2005 | Cosendai et al. | |
| 2005/0149148 A1* | 7/2005 | King ................. | A61N 1/36007 607/70 |
| 2007/0043400 A1 | 2/2007 | Donders et al. | |
| 2007/0142863 A1 | 6/2007 | Bradley | |
| 2007/0185549 A1 | 8/2007 | Zdeblick | |

OTHER PUBLICATIONS

International Search Report for PCT/US08/012209, mailed Jan. 9, 2009, 1 page.

* cited by examiner

*Primary Examiner* — Eric D. Bertram
(74) *Attorney, Agent, or Firm* — Tarolli, Sundheim, Covell & Tummino LLP

(57) ABSTRACT

A method of blocking signal transmission through a nerve with reduced onset activity includes applying an HFAC to an axon of a nerve to block the transmission of signals through the axon. The method may also include applying a direct current (DC) to the axon, increasing the amplitude of the DC over time to a predetermined amplitude, applying the HFAC, and then decreasing the DC. The method may also include temporarily reducing the amplitude of the HFAC to permit the transmission of signals through the axon and subsequently increasing the amplitude to block transmission without triggering an onset response. The method may also include temporarily applying an unbalanced charge to the nerve and then balancing the charge over time.

9 Claims, 8 Drawing Sheets

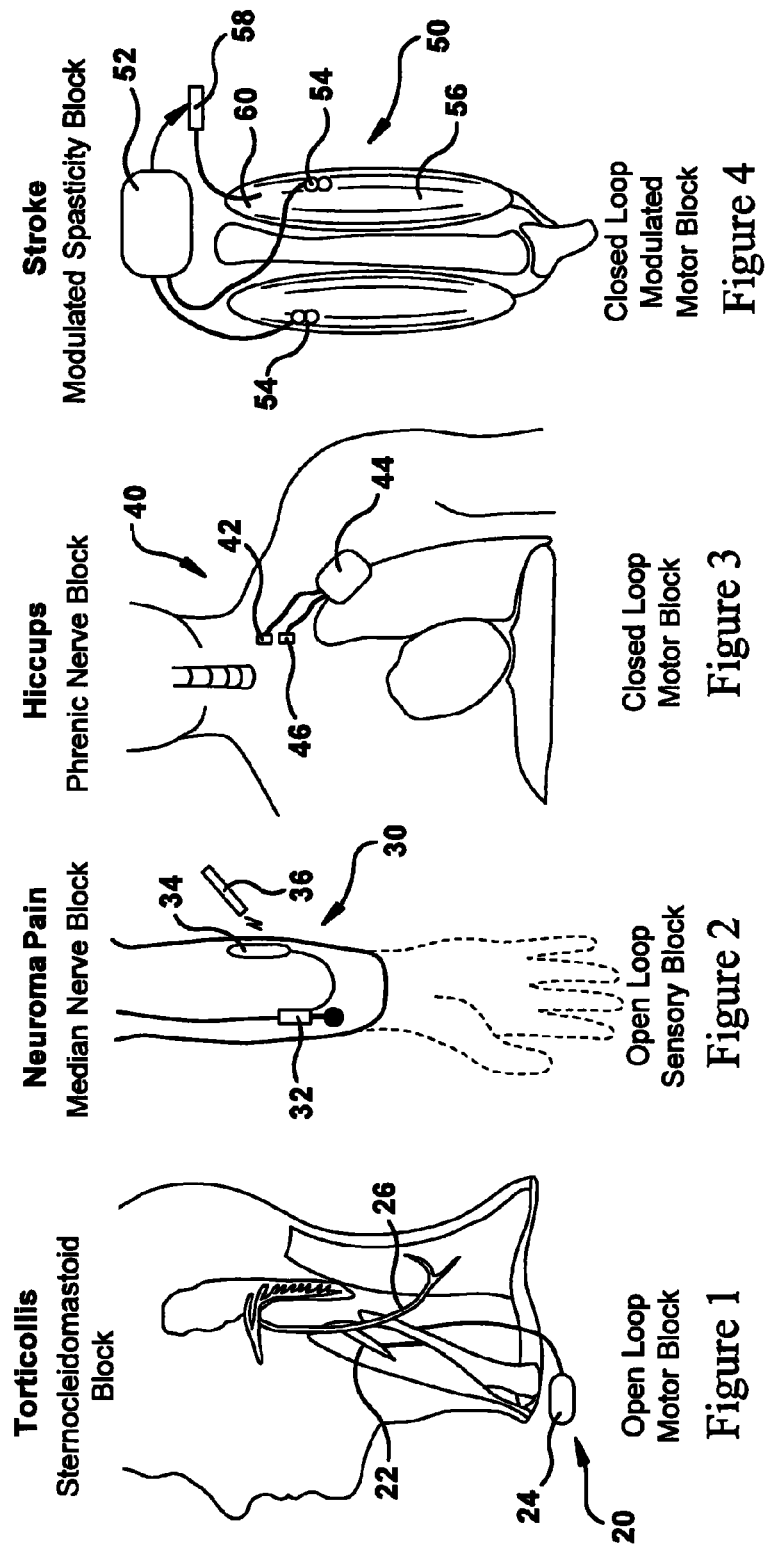

ONSET-MITIGATING HIGH-FREQUENCY NERVE BLOCK

CROSS REFERENCE TO RELATED APPLICATIONS

This application is a divisional application of U.S. patent application Ser. No. 12/739,413, filed Apr. 23, 2010, now U.S. Pat. No. 8,983,614, which is a National Stage Application of PCT/US08/12209, filed Oct. 28, 2008, which claims the benefit of U.S. Provisional Patent Application No. 60/983,420, filed Oct. 29, 2007. The entirety of each of the aforementioned applications is hereby incorporated by reference for all purposes.

FEDERAL FUNDING NOTICE

This invention was made with government support under grant No. EB002091, awarded by the NIH-National Institute of Biomedical Imaging and Bioengineering. The government has certain rights in the invention.

COPYRIGHT NOTICE

A portion of the disclosure of this patent document contains material subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

Unwanted and/or uncoordinated generation of nerve impulses may be a disabling factor in some medical conditions. For example, uncoordinated motor signals may produce spasticity in stroke, cerebral palsy, multiple sclerosis, and other conditions. The uncoordinated signals may result in the inability to make desired functional movements. Involuntary motor signals in conditions including tics, choreas, and so on, may produce unwanted movements. Additionally, unwanted sensory signals can cause pain. Conventional approaches have attempted to intercept unwanted or uncoordinated nerve impulses along the nerves on which they travel to attempt to reduce and/or eliminate the disabling condition.

Conventional approaches associated with treating these conditions have produced unsatisfactory results. For example, drug treatments may have produced unwanted side-effects, may have acted globally on the body rather than specifically on a specific nerve, and may have been neither quick acting nor quickly reversible. While chemical treatments (e.g., Botox, phenol blocks), may be applied more specifically, they may have been destructive to the nerve, may have required reapplication, and may not have been quickly reversible. Other conventional treatments for pain (e.g., transcutaneous electrical nerve stimulation (TENS), implantable pain stimulators) have also produced sub-optimal results.

Both alternating current (AC) and direct current (DC) nerve stimulation are known in the art. The inhibitory effect of high-frequency alternating current (HFAC) on nerves has been reported since the early 1900's. Additionally, DC electrical nerve stimulation has been illustrated to produce a nearly complete block of nerve activity. However, conventional DC stimulation has damaged both body tissues and/or electrodes when delivered over prolonged periods of time. Thus conventional DC stimulation has been unsuitable for certain applications. The damage caused by a DC nerve block is due, at least in part, to unbalanced charge applied to the nerve. HFAC, which delivers a zero net charge to the tissue is likely to be safer as a method for nerve block. However, when HFAC is delivered to a nerve, it causes a burst of activity in the nerve that is undesirable and likely to be painful. The burst of activity produced by HFAC is referred to as the onset activity.

SUMMARY

This application concerns apparatus, systems, and methods for blocking signal transmission through a nerve without generating activity in the nerve outside of the system. One example concerns applying a DC and a high-frequency alternating current (HFAC) in a combination(s) that cancels, prevents or minimizes an undesirable reaction of the nerve to the onset of the HFAC based nerve conduction block.

One example method of blocking nerve signal transmission comprises applying a DC at a first amplitude to the axon of a nerve and then increasing the amplitude of the DC over a period of time to a predetermined second amplitude. After the DC has reached the second amplitude, the HFAC is applied. After the HFAC is applied, the amplitude of the DC is decreased.

Another example method of blocking nerve signal transmission comprises applying the HFAC at a first amplitude that blocks signal transmission. The method includes temporarily reducing the HFAC amplitude to permit the transmission of signals through the axon. The method also includes subsequently selectively increasing the HFAC amplitude to again block transmission. In this example, the subsequent blocking occurs without triggering an onset response.

Another example method of blocking nerve signal transmission comprises temporarily applying an unbalanced charge to an axon of a nerve. In one example, applying an unbalanced charge may include applying an unbalanced charge AC to the axon and balancing the charge over time. In another example, applying an unbalanced charge may include applying an unbalanced charge AC to the axon and varying the amplitude over time while also balancing the charge. In another example, applying an unbalanced charge may include applying a DC charge of increasing amplitude and, after reaching a predetermined amplitude, applying an unbalanced AC and gradually increasing the AC amplitude and AC charge balance over time.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 1 illustrates an open loop apparatus associated with a nerve block.

FIG. 2 illustrates an open loop apparatus associated with a nerve block.

FIG. 3 illustrates a closed loop apparatus associated with a nerve block.

FIG. 4 illustrates a closed loop apparatus associated with a nerve block.

DETAILED DESCRIPTION

Figure 5:
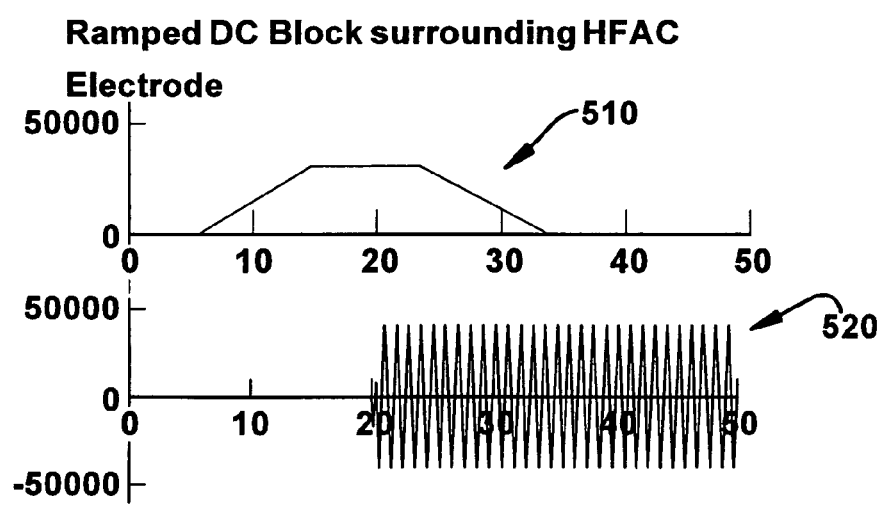
FIG. 5 illustrates a combination of DC and HFAC associated with an onset-mitigating nerve block.

Example systems, methods, and apparatus produce a nerve block using HFAC waveforms. The block produced by HFAC waveforms is a conduction block in the nerve, and not simply a fatigue block. The block may be referred to as a "nerve conduction block". The block is not a result of the nerve being stimulated until it is too fatigued to respond and can no longer recover before the next pulse. The HFAC waveforms block conduction through the nerves by blocking signal transmission through the axon. Unlike a chemical block, which interrupts the transmission of a chemical signal from the ends of one nerve to the ends of another, an HFAC nerve conduction block prevents the axon of the nerve from transmitting any signals past the area of the block. The block is based on how electrical currents produce activation or block nerve conduction through their influence on the voltage-gated ion channels in the nerve membrane.

HFAC waveforms depolarize the nerve membrane causing the inactivation gates to close. The biophysical mechanism that produces the onset response is based on the effect of the depolarizing current on the nerve membrane. In general, depolarizing the nerve membrane triggers the opening of the fast sodium ion channels, initiating an action potential. Placing the nerve in an alternating current depolarizing field, however, actually results in conduction failure, because it forces the inactivation sodium ion gate to remain closed. Therefore, depolarization is involved in both activating and blocking nerve conduction. It is this dichotomy of action that produces the onset response.

There are two phases of the onset response. The first phase is a summated twitch response that occurs in those nerve fibers to which an AC near or above the block threshold is being applied. The "block threshold" is defined as the voltage below which a complete block is not obtained. The block threshold increases with frequency. The block threshold generally varies inversely with axon diameter. In addition, the block threshold varies approximately as the square of the perpendicular distance to the axon from the electrode. When the electrode is closer than one millimeter to the axon, the electrode position along the length of the axon also affects the amplitude of the block threshold.

Once the initial firing is over, which generally occurs in approximately 20 milliseconds, these axons are blocked. The second phase is a period of repetitive firing that can last many seconds. This second phase is not always present and tends to be significantly reduced with higher amplitudes of HFAC. This second phase may be due to the repetitive firing of axons that are on the fringes of the current spread from the electrode. Eventually, the firing in these fibers comes to a stop. The amplitude of the electrical signal decreases with distance from the electrode. A decrease in the second phase at higher amplitudes may be related to higher amplitudes placing more of the nerve fiber completely within the region that provides sufficient amplitude to produce the block. Since the current gradients are sharper, fewer fibers are within the amplitude region that produces repetitive firing.

Eliminating the undesired onset entirely involves eliminating both phases of the onset response. The repetitive phase can be reduced by adjusting amplitude and frequency. For example, a 30 kilohertz, 10 volts peak-to-peak sinusoidal waveform may eliminate the repetitive phase. Generally it is not possible to eliminate the entire onset response by changing frequency and amplitude alone.

Recall that the damage caused by a DC nerve block is due to the charge imbalance applied to the nerve. Therefore, example systems, methods, and apparatus balance charge using AC. Balancing the charge prevents and/or minimizes damage caused by unbalanced charges. A pure AC nerve block typically produces an onset response from the nerve on start-up. Thus some examples described and claimed herein first apply DC to a nerve and then subsequently apply an HFAC nerve block. The combination of DC and HFAC is crafted to prevent the occurrence of the onset response in the nerve to be blocked. Conventional approaches employing an HFAC waveform as a nerve conduction block produce the onset response that is typically unacceptable in the application of HFAC waveforms to human patients.

"High-frequency", as used herein with reference to alternating current (e.g., HFAC), refers to frequencies above approximately 1 kiloHertz. In some examples, high-frequency refers more specifically to 5 to 50 kiloHertz. Example systems, methods, and apparatus described herein employ a waveform having an amplitude of approximately 4 to 10 volts per pulse. Example systems, methods, and apparatus described herein employ a waveform having a current of about 1 milliamp to about 12 milliamps. Within these voltage and amperage ranges, a waveform having a higher frequency will generally require a higher amplitude to provide an effective block.

Examples described herein may have application in areas including motor nerve block, sensory nerve block, and autonomic block. Additionally, examples described herein may be applied in an open loop configuration where the block is controlled through a switch and/or in a closed loop configuration where the block is controlled automatically through a sensor(s).

FIG. 1 illustrates an example apparatus 20 associated with blocking transmission in a nerve. Apparatus 20 includes an electrode 22 connected to a controller 24 suitable for delivering HFAC and/or both DC and HFAC signals to a nerve 26. Apparatus 20 has an open loop configuration where the controller 24 includes a switch to control application of the block. This configuration of apparatus 20 may facilitate controlling, for example, muscle spasticity. Apparatus 20 may apply the HFAC through a set of HFAC electrodes 22 on the motor branches of the nerve 26. This facilitates targeting a specific muscle associated with nerve 26 to facilitate relaxing that muscle. In one example, apparatus 20 may provide a stemocleidomastoid block useful for treating torticollis.

FIG. 2 illustrates an apparatus 30 used, for example, to block neuroma pain, pain associated with a missing appendage, pain associated with a damaged appendage, and so on. Apparatus 30 may, therefore, produce a median nerve block. Apparatus 30 comprises an HFAC blocking electrode 32 and an implantable controller 34. The blocking electrode 32 may be positioned adjacent to a nerve proximal to a neuroma. In this application, the nerve block can be delivered continuously, can be triggered using an external signal device 36, and so on.

FIG. 3 illustrates an apparatus 40 that provides a motor block. The motor block may be triggered by a recorded signal. Apparatus 40 is a closed-loop system and is illustrated in an application to block intractable hiccups. Indicia (e.g., biological signals) associated with an impending hiccup may be recorded via a sensor 42. In one example, the indicia may appear as a large signal on the phrenic nerve. This signal may control triggering a controller 44 to apply an HFAC block to the phrenic nerve. The block may be administered using an electrode 46 adjacent to the phrenic nerve. The HFAC block prevents diaphragm contraction for a brief period, which interrupts and/or preempts signals that cause the diaphragm to hiccup.

Signals associated with moving a muscle may be recorded when a user intends to move that muscle. The signals may be propagated along a nerve. These signals may facilitate controlling spastic muscles in stroke patients, patients having multiple sclerosis, patients having cerebral palsy, and so on. In one example, signals may be recorded from both spastic muscles and non-spastic muscles. Therefore, FIG. 4 illustrates an apparatus 50 that includes a controller 52. Controller 52 comprises a recorder for recording and processing signals from sensors 54 in muscles 56 and/or nerves that control muscles 56. The controller 52 controls a signal generator 58 to apply an HFAC waveform to an electrode 60 adjacent a nerve that controls muscles 56.

Spasticity reduces function in muscles. However, improved function may be achieved by producing a partial block of undesired motor activity. Thus, example apparatus, methods, and so on, may be configured to quickly reverse an HFAC block. In one example, improved function may be achieved by combining an HFAC block with an intelligent control system that varies the nerve block based on sensed activity including, for example, nerve activity, muscle activity, and so on.

Example systems, methods, and apparatus may produce at least three categories of no-onset and/or onset-mitigating HFAC block solutions. In a first example, separate "onset-blocking" electrodes apply a DC block on either side of the HFAC electrodes. In a second example, charge-balanced transitory variations of a HFAC waveform produce a no-onset and/or onset-mitigating HFAC block. In a third example, charge-imbalanced transitory variations of the HFAC waveform produce a no-onset and/or onset-mitigating HFAC block.

FIG. 5 illustrates a combination of a DC waveform 510 and an HFAC waveform 520 to produce an HFAC block. In one example, the DC waveform 510 and the HFAC waveform 520 are provided using separate electrodes. In one example, DC waveforms and HFAC waveforms are provided through a single set of electrodes. The charge in the DC waveform 510 is ramped up in region 512 before the HFAC waveform 520 is turned on. The DC waveform 510 in region 514 has amplitude sufficient to provide a DC block, which will block the onset response from the HFAC waveform 520. The DC waveform 510 is ramped down in region 514 once the onset activity is complete. Unlike the charge-imbalanced waveforms discussed below, this ramped DC waveform 510 allows the onset activity caused by the HFAC waveform 520 to occur, but prevents that onset activity from propagating. Although continuous delivery of DC at this level can damage the electrodes that deliver the DC block and nearby tissue, infrequent brief application of the DC block may not cause such damage. In one example, the DC block is delivered for approximately 100 to 200 milliseconds each time the HFAC block is turned on. Since a DC block can be produced by monopolar electrodes, in one example the DC electrodes and the HFAC electrodes may be combined into a single five-pole nerve cuff electrode. This five-pole nerve cuff electrode may include two outer electrodes for direct current and three inner electrodes for HFAC. A further form of the electrode may utilize a three-pole nerve cuff electrode in which the DC and HFAC are superimposed on the outer electrodes.

Figure 6:
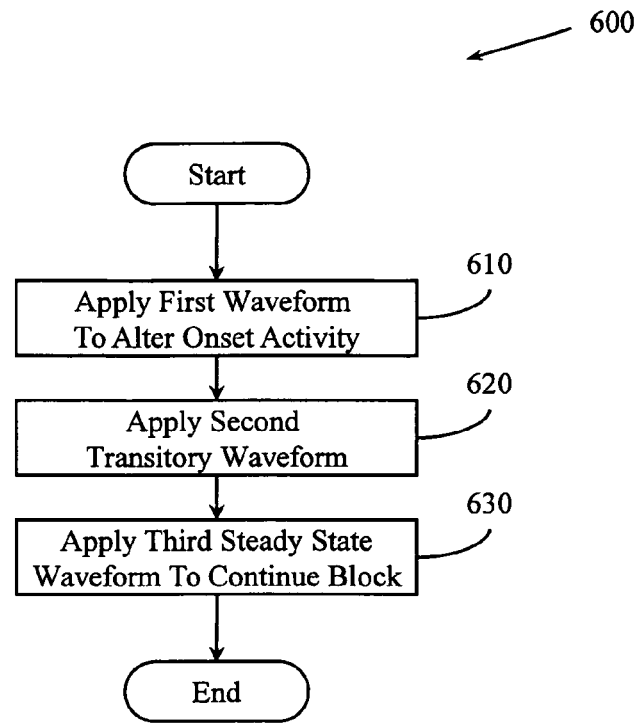
FIG. 6 illustrates a method associated with an onset-mitigating nerve block.

FIG. 6 illustrates a method associated with onset-mitigating HFAC. Method 600 includes, at 610, applying a first waveform to a nerve to alter onset activity in that nerve. Method 600 also includes, at 620, applying a second transitory wave to the nerve. Method 600 also includes, at 630, applying a third steady state wave to the nerve to continue the HFAC block in the nerve.

Figure 7:
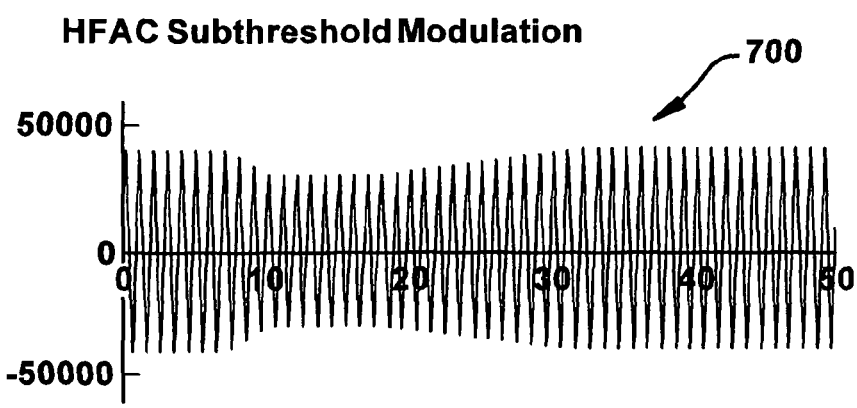
FIG. 7 illustrates an HFAC associated with an onset-mitigating nerve block.

FIG. 7 illustrates a charge-balanced approach that includes applying a rapid onset block above the block threshold and accepting the initial onset response. In this approach, the amplitude is then lowered below the block threshold but maintained high enough to avoid the zone of repetitive firing. The previously blocked nerve can conduct normally through the region of HFAC delivery at this amplitude. Then, when a block is desired, the amplitude is ramped up to the block threshold. In this example, the block can be achieved without further firing and thus with no additional onset response. This method maintains a zero net charge but requires that the waveform be delivered even when a block is not needed. In this example, the onset still occurs when the system is first turned on. This method may be employed, for example, in stroke applications. In this environment there may be periods of rapid modulation of the block during functional tasks. This amplitude-modulation method may be suitable in this environment because it can produce a quick transition between block and no-block conditions. During periods of inactivity, the block can be turned off. However the block can be re-initiated prior to activity using one of the onset-blocking alternatives.

Figure 8:
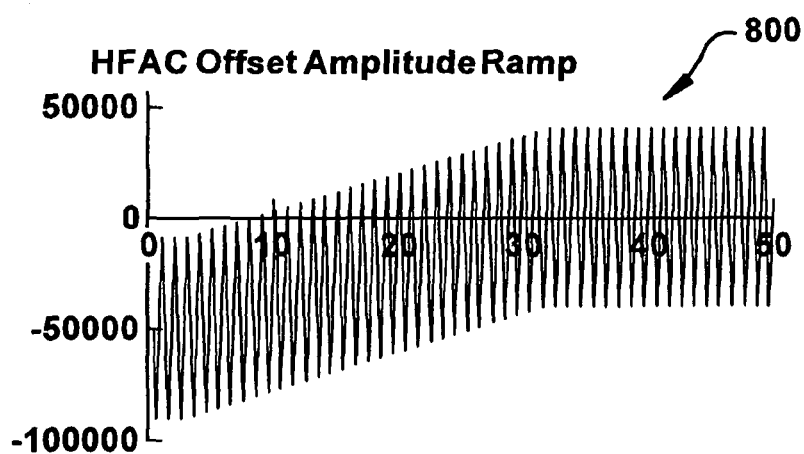
FIG. 8 illustrates an HFAC associated with an onset-mitigating nerve block.

FIG. 8 illustrates applying an HFAC waveform 810 with an initial offset charge. The HFAC waveform 810 is then ramped up to a charge-balanced average. This type of charge-imbalanced transitory variation may eliminate the onset response. The HFAC waveform 810 is initially charge-imbalanced, and then transitions to a charge-balanced waveform over a period of tens of milliseconds or longer. This achieves a brief period of effective direct current. In FIG. 8, both the amplitude of the HFAC waveform 810 and the amount of offset are ramped toward the charge-balanced waveform.

Figure 9:
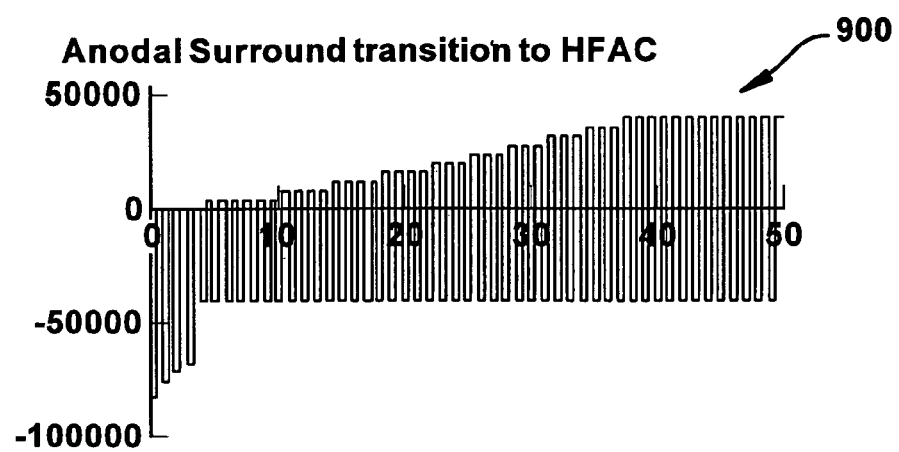
FIG. 9 illustrates an HFAC associated with an onset-mitigating nerve block.

FIG. 9 illustrates another HFAC waveform 910 for producing a nerve block. This is a second example that uses charge-imbalanced waveforms to eliminate and/or mitigate the onset response and relies on the virtual electrode zones that develop during monophasic activation. For sufficiently large depolarizing monophasic pulses, the initial action potentials associated with an onset response are blocked in the adjacent virtual anodes. This may be referred to as an anodal surround block. Using this feature, the HFAC block will start with a monophasic waveform that produces an anodal surround block starting with the first pulse delivered. Subsequently, the charge-imbalance is decreased to achieve balance. The steady state condition is a charge-balanced HFAC waveform that maintains the block. The transitory portion of this waveform lasts approximately 100 milliseconds or longer and is robust across axon diameters and electrode distances.

Figure 10:
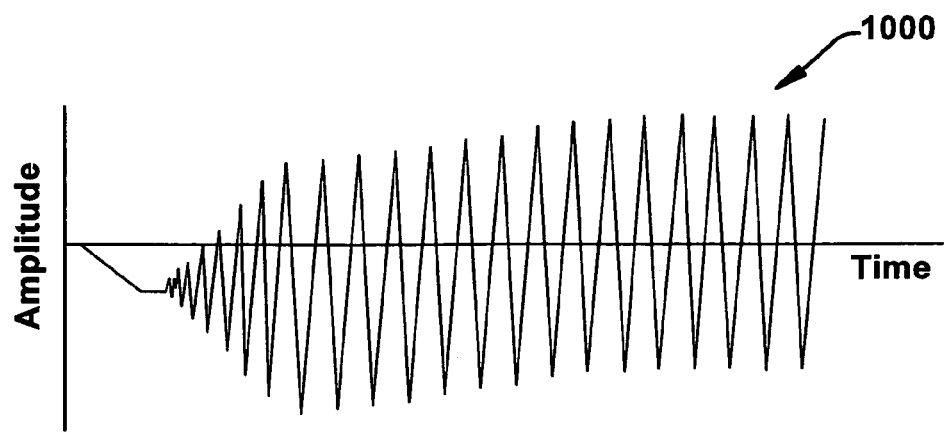
FIG. 10 illustrates an HFAC associated with an onset-mitigating nerve block.

FIG. 10 illustrates another waveform 1010 for producing a nerve block. Waveform 1010 starts with a ramped cathodic or anodic direct current. While the term "ramped" is used herein, one skilled in the art will appreciate that more generally the waveform may include linear and/or non-linear increases in DC and/or HFAC amplitude. Thus, "ramped" or "ramping" are not to be interpreted as requiring a linear increase up to some level. An HFAC waveform is started after a period where the ramped direct current is applied. The HFAC waveform has its amplitude increased until it reaches a block threshold. At this point, the DC offset is ramped down until the whole waveform is charge-balanced, thus allowing the HFAC block to be established without onset action potentials. In one example, the DC offset peak is in the range of approximately ten percent of the HFAC amplitude. In one example, the total time during which the DC is applied is about 80 milliseconds. The total time includes the DC ramp-up, the DC plateau, and the DC ramp down.

Some portions of the detailed descriptions that follow are presented in terms of algorithms. These algorithmic descriptions and representations are used by those skilled in the art to convey the substance of their work to others. An algorithm, here and generally, is conceived to be a sequence of operations that produce a result. The operations may include physical manipulations of physical quantities. The physical manipulations create a concrete, tangible, useful, real-world result.

Example methods may be better appreciated with reference to flow diagrams. For purposes of simplicity of explanation, the illustrated methodologies are shown and described as a series of blocks. However, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 11:
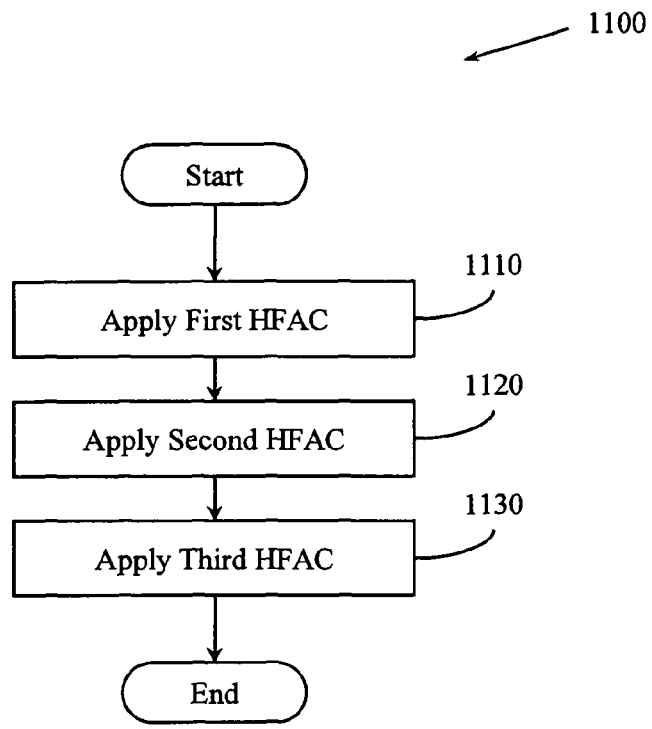
FIG. 11 illustrates a method associated with providing a nerve conduction block where an onset response is mitigated.

FIG. 11 illustrates a method 1100 associated with an HFAC nerve conduction block. Method 1100 includes, at 1110, applying a first HFAC to an axon of a nerve. The first HFAC will have a first amplitude, a first frequency, and a first current. The combination of amplitude, frequency, and current is configured to produce a nerve conduction block in the axon. Recall that a nerve conduction block actually blocks transmission of signals through the axon.

Method 1100 also includes, at 1120, applying a second HFAC to the axon. The second HFAC has a second amplitude, a second frequency, and a second current. This combination of amplitude, frequency, and current will not produce a nerve conduction block in the axon. However, this combination of amplitude, frequency, and current will prevent the occurrence of an onset condition in the axon upon the application of a third HFAC that is sufficient to produce a nerve conduction block in the axon. One skilled in the art will appreciate that the third HFAC may be similar to or identical to the first HFAC.

Thus, method 1100 also includes, at 1130, applying a third HFAC to the axon. The third HFAC has a third amplitude, a third frequency, and a third current. This combination of the third amplitude, the third frequency, and the third current will produce a nerve conduction block in the axon. However, it will do so with less onset activity than would otherwise be incurred.

In one example, all three frequencies are in the range of 1 kiloHertz to 100 kiloHertz. In one example, the first and third frequencies are the same, and the second frequency is different. In one example, the first amplitude and the third amplitude are in the range of 4 volts peak-to-peak to 10 volts peak-to-peak. In one example, the first current and the third current are in the range of 1 milliamp to 12 milliamps. One skilled in the art will appreciate that various combinations of frequency, amplitude, and current can produce a nerve conduction block. The nerve conduction block may be, for example, a motor nerve block, a sensory nerve block, an autonomic block, and so on. The nerve conduction block may be applied to treat symptoms of torticollis, neuroma pain, hiccups, cerebral palsy, muscular dystrophy, stroke, and so on. The nerve conduction block may be, for example, a stemocleidomastoid block, a median nerve block, a phrenic nerve block, a modulated spasticity block, and so on.

Method 1100 may be controlled to selectively apply the first HFAC, the second HFAC, and/or the third HFAC based, at least in part, on a control signal received from an open loop control apparatus. The control signal may be received, for example, from a switch. Similarly, method 1100 may be controlled to selectively apply the first HFAC, the second HFAC, and/or the third HFAC based, at least in part, on a control signal received from a closed loop control apparatus. The closed loop control apparatus may be, for example, a sensor. Method 1100 may also be controlled to selectively alter the frequency, voltage, and current of an HFAC based on inputs from an open loop apparatus and/or a closed loop apparatus.

In different examples, the first HFAC, the second HFAC, and/or the third HFAC may initially be unbalanced with respect to charge. Thus, method 1100 may include balancing, over a period of time, the charge of an initially unbalanced HFAC. In one example, method 1100 may include varying the amplitude of the unbalanced HFAC over time while the charge is being balanced.

Figure 12:
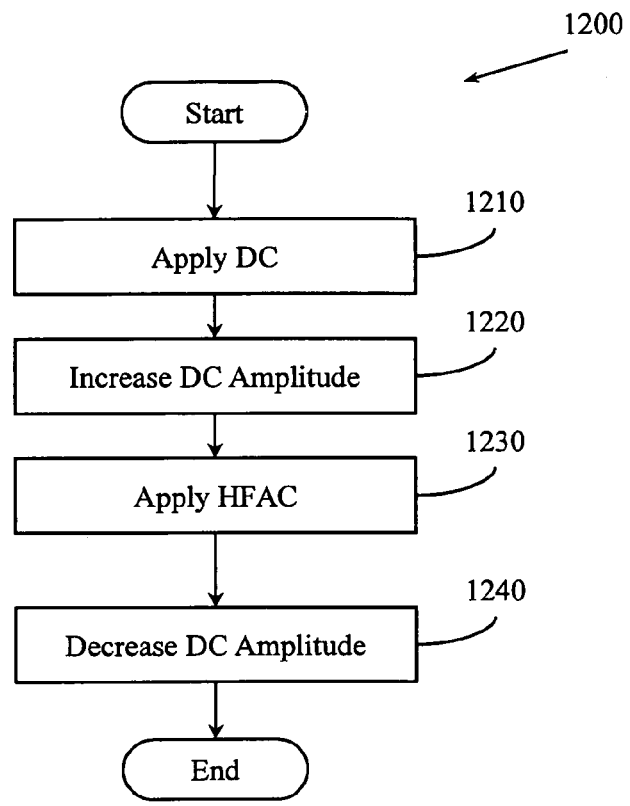
FIG. 12 illustrates a method associated with providing a nerve conduction block where an onset response is mitigated.

FIG. 12 illustrates a method 1200 associated with an HFAC nerve conduction block. Method 1200 includes, at 1210, first applying a direct current (DC) to an axon of a nerve. This DC will have a first DC amplitude that is not sufficient to produce a nerve block in the axon. Method 1200 then proceeds, at 1220, to increase the first DC amplitude over a period of time. The first DC amplitude is increased to a second DC amplitude that is sufficient to produce a nerve block in the axon.

Method 1200 then proceeds, at 1230, to apply an HFAC to the axon. The HFAC has an HFAC amplitude, an HFAC frequency, and an HFAC current. The combination of frequency, amplitude, and current is designed to produce a nerve conduction block in the axon. Note that the HFAC is applied after the DC has been ramped up to a desired level. Method 1200 then proceeds, at 1240, to decrease the second DC amplitude to a third DC amplitude over a period of time. The DC having the third DC amplitude is not sufficient to produce a nerve block in the axon. Thus, method 1200 provides a combination of the DC and the HFAC in an order that reduces an onset activity that is observed in the nerve either proximally or distally to the blocking electrode or electrodes.

In one example, the DC offset peak is between five percent and fifteen percent of the HFAC amplitude. In one example, the first period of time and the second period of time during which the DC is ramped up and then ramped down collectively comprise less than 80 milliseconds. In another example, the first period of time is between 100 milliseconds and 200 milliseconds, and the second period of time is between 100 milliseconds and 200 milliseconds.

Figure 13:
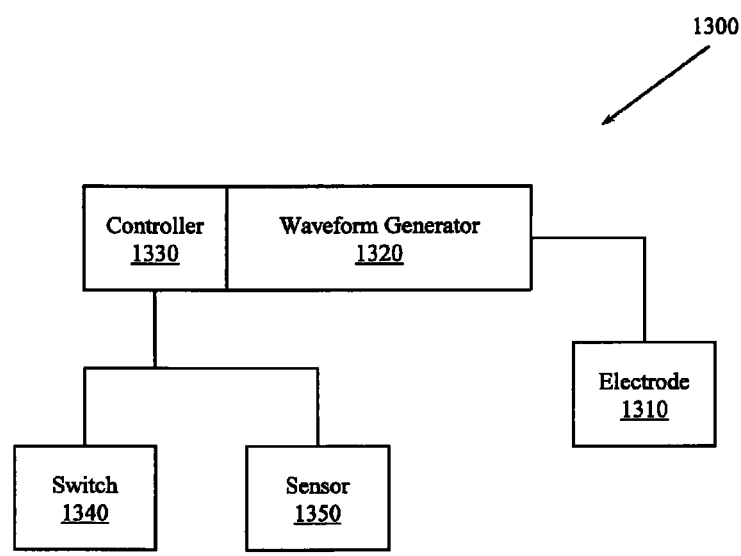
FIG. 13 illustrates an apparatus associated with providing a nerve conduction block where an onset response is mitigated.

FIG. 13 illustrates an apparatus 1300 associated with an HFAC nerve conduction block. Apparatus 1300 includes an electrode 1310 and a waveform generator 1320 connected to the electrode. Apparatus 1300 also includes a controller 1330. Controller 1330 is to control the waveform generator 1320 to apply DC and/or HFAC as described in connection with method 1100 (FIG. 11) and/or method 1200 (FIG. 12). In one example, apparatus 1300 may include a switch 1340 to selectively control the controller 1330 and/or the waveform generator 1320. In another example, apparatus 1300 may include a sensor 1350 to selectively control the controller 1330 and/or the waveform generator 1320. In one example, the electrode 1310 may have five nodes. The five nodes may include a set of two inner nodes for applying an HFAC and a set of three outer nodes for applying a DC.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, and so on (e.g., the data store may store only A, only B, only C, A&B, A&C, B&C, A&B&C, A&A&A, A&A&B, A&A&B&B, A&A&B&B&C, A&A&B&B&C&C, and so on). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. An apparatus, comprising:
   an electrode;
   a waveform generator connected to the electrode; and
   a controller configured to:
   control the waveform generator to first apply a direct current (DC) to a nerve, the DC having a first DC amplitude not sufficient to produce a nerve block in the axon;
   then control the waveform generator to change the first DC amplitude to a second DC amplitude sufficient to produce a conduction block in the nerve;
   then control the waveform generator to apply a high frequency alternating current (HFAC) to the nerve, the HFAC having an HFAC amplitude and an HFAC frequency, the HFAC being configured to produce a conduction block in the nerve; and
   then, after a time period, control the waveform generator to alter the DC over a second period of time by changing the second DC amplitude to a third DC amplitude not sufficient to produce a conduction block in the nerve;
   where the DC with the second amplitude and the HFAC are applied at the same time, so that the DC blocks an onset activity in the nerve associated with the HFAC.

2. The apparatus of claim 1, the electrode comprising a four node electrode, the four node electrode comprising a set of two inner nodes for applying the HFAC and a set of two outer nodes for applying the DC.

3. The apparatus of claim 1, the electrode comprising a three node electrode, the three nodes comprising a set of two outer nodes for applying both the HFAC and DC together, and the center node for applying the HFAC only.

4. The apparatus of claim 1, where the HFAC frequency is in the range of 1 kiloHertz to 100 kiloHertz.

5. The apparatus of claim 1, where the nerve conduction block is one of: a motor nerve block, a sensing nerve block, an autonomic block, a sternocleidomastoid block, a median nerve block, a phrenic nerve block, a celiac plexus nerve block, and a modulated spasticity block, and where the nerve conduction block is applied to treat symptoms of one or more of, torticollis, neuroma pain, hiccups, muscular dystrophy, cancer pain, post-operative pain, chronic pain, pain, and stroke.

6. The apparatus of claim 1, wherein the time period is sufficient for the DC with the second amplitude to block an onset activity caused by the HFAC.

7. The apparatus of claim 1, wherein the time period comprises one second or less.

8. The apparatus of claim 1, wherein the time period is between 1 seconds and 5 seconds.

9. The apparatus of claim 1, wherein the time period ends after the onset activity caused by the HFAC ends.

* * * * *